US00PP20430P2

(12) United States Plant Patent
Pieters

(10) Patent No.: US PP20,430 P2
(45) Date of Patent: Oct. 20, 2009

(54) ***CHRYSANTHEMUM* PLANT NAMED 'PPP BELG 07'**

(50) Latin Name: *Chrysanthemum morifolium*
Varietal Denomination: PPP BELG 07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,846

(22) Filed: Jul. 18, 2008

(51) Int. Cl.
*A01H 5/00* (2006.01)

(52) U.S. Cl. ..... Plt./287
(58) Field of Classification Search ..... Plt./287, Plt./292, 293
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by small decorative type inflorescences, consistent flowering response to short days, blooming consistently after 49 days of short day length, dark lilac ray florets, free branching habit, and a consistent natural season flowering habit during the first week of September.

1 Drawing Sheet

Latin name of the genus and species: *Chrysanthemum morifolium.*

Variety denomination: 'PPP BELG 07'.

BACKGROUND OF THE INVENTION

The new cultivar 'PPP BELG 07' is a product of a cross between the male parent 'GEDI ONE GAL' (U.S. Plant Pat. No. 13,807) and the female parent 'Emily' (U.S. Plant Pat. No. 7,754). The new cultivar was discovered and selected by Dirk Pieters in September of 2001 in Oostnieuwkerke, Belgium.

Asexual reproduction of the new cultivar 'PPP BELG 07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP BELG 07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP BELG 07.' These characteristics in combination distinguish 'PPP BELG 07' as a new and distinct *Chrysanthemum* cultivar:

1. Small, dark lilac, decorative-type inflorescences;
2. Consistent natural season flowering habit during the first week of September;
3. Free branching habit; and
4. Consistent flowering response to short days, blooming consistently after 49 days of short day length.

Plants of the new cultivar 'PPP BELG 07' are similar to plants of the male parent variety, 'GEDI ONE GAL' in most horticultural characteristics, however plants of the new cultivar 'PPP BELG 07' are shorter. Also, the new cultivar 'PPP BELG 07' has a smaller inflorescence diameter and longer inflorescence longevity. Additionally, the ray florets of 'PPP BELG 07' are a different color than the male parent. Finally, 'PPP BELG 07' naturally blooms three to four weeks earlier than the male parent 'GEDI ONE GAL.'

Plants of the new cultivar 'PPP BELG 07' are similar to plants of the female parent variety, 'Emily' in most horticultural characteristics, however plants of the new cultivar 'PPP BELG 07' are shorter but have a wider plant spread. Also, the new cultivar 'PPP BELG 07' has a smaller inflorescence diameter. Additionally, the ray florets of 'PPP BELG 07' are a different color than the female parent. Finally, 'PPP BELG 07' naturally blooms one week later than the female parent 'Emily.'

In comparison to the commercially available variety 'GEDI TWO PAD' (U.S. Plant Pat. No. 14,501), 'PPP BELG 07' is shorter and wider. Additionally, the new variety 'PPP BELG 07' has a smaller inflorescence diameter and darker purple ray florets. Further, the new variety 'PPP BELG 07' has more ray florets per inflorescence. Finally, 'PPP BELG 07' has longer inflorescence longevity.

BRIEF DESCRIPTION OF THE PHOTOGRAPH

The accompanying photograph illustrates in full color a typical plant of 'PPP BELG 07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP BELG 07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP BELG 07.'

Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 21.5 cm.
Plant spread: Approximately 40 cm.
Growth rate: Moderate.
Branching characteristics: Free Branching.
Length of lateral branches: Approximately 16 cm.
Number of leaves per lateral branch: Approximately 20.
Age of plant described: Approximately 138 days.

FOLIAGE

Leaf:
- *Arrangement.*—Alternate single.
- *Average length.*—Approximately 3 cm.
- *Average width.*—Approximately 2.5 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1.3 cm.
- *Color.*—Young foliage upper side: Near Yellow-Green 147A. Young foliage under side: Near Green 137D. Mature foliage upper side: Near Yellow-Green 147A. Mature foliage under side: Near Green 137C.
- *Venation.*—Type: Palmately net. Venation color upper side: Near Green 138A. Venation color under side: Near Green 138C.

Petiole:
- *Average length.*—Approximately 1 cm.
- *Color.*—Near Green 138A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately first week in September.
- *Number of inflorescences per lateral branch.*—Approximately 23.
- *Inflorescence diameter.*—Approximately 2.9 cm.
- *Inflorescence depth.*—Approximately 1.1 cm.
- *Inflorescence longevity on plant.*—Approximately 28 to 34 days.
- *Persistence.*—Persistent.

Ray florets:
- *Appearance.*—Matte.
- *Texture.*—Smooth.
- *Average number of ray florets per inflorescence.*—270.
- *Shape.*—Obelliptic.
- *Aspect.*—Flat.
- *Margin.*—Entire.
- *Apex.*—Obtuse.
- *Length.*'Approximately 1.1 cm.
- *Width.*—Approximately 0.4 cm.
- *Color.*—Upper surface at first opening: Near Red-Purple 61A. Upper surface at maturity: Near Red-Purple 70A. Upper surface at fading: Near Purple 75C. Under surface at first opening: Near Red-Purple 71A. Under surface at maturity: Near Red-Purple 74C. Under surface at fading: Near Purple 78C.

Disc florets:
- *Appearance.*—Shiny.
- *Texture.*—Smooth.
- *Average number of florets per disc.*—Approximately 3.
- *Shape.*—Cylindric.
- *Apex.*—Obtuse.
- *Average length.*—Approximately 0.3 cm.
- *Average width.*—Approximately 0.1 cm.
- *Color.*—At first opening: Near Yellow-Green 154C. At maturity: Near Yellow 13A. At fading: Near Yellow 13A.

Peduncle:
- *Length.*—At terminal end (shortest): Approximately 3.8 cm. At lateral end (longest): Approximately 4.6 cm.
- *Angle to stem.*—Acute.
- *Strength.*—Moderate.
- *Color.*—Near Green 138B.
- *Habit.*—Upright.
- *Diameter.*—Approximately 0.2 cm.
- *Surface texture.*—Lightly pubescent.

Inflorescence bud:
- *Length.*—Approximately 0.8 cm.
- *Diameter.*—Approximately 0.5 cm.
- *Form.*—Globular.
- *Color.*—Near Red-Purple 71A.

Involucral bracts (phyllaries):
- *Appearance.*—Matte.
- *Texture.*—Lightly pubescent.
- *Number.*—Approximately 27.
- *Shape.*—Lanceolate.
- *Margin.*—Entire.
- *Apex.*—Obtuse.
- *Length.*—Approximately 0.5 cm.
- *Width.*—Approximately 0.1 cm.
- *Color.*—Upper side. Near Green 138A. Under side: Near Green 138C.

REPRODUCTIVE ORGANS

Ray florets:
- *Number of pistils per floret.*—1.
- *Stigma shape.*—2 branched.
- *Stigma color.*—Near Yellow 13A.
- *Style color.*—Near Green-Yellow 1C.
- *Style length.*—Approximately 0.2 cm.
- *Stamens.*—Absent.

Disc florets:
- *Number of pistils per floret.*—1.
- *Stigma shape.*—Cylindric.
- *Stigma color.*—Near Yellow 13A.
- *Style length.*—Approximately 0.3 cm.
- *Style color.*—Near Green-Yellow 1C.
- *Number of stamens per floret.*—Approximately 5.
- *Anther shape.*—Tubular.
- *Anther color.*—Near Yellow 13A.
- *Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP BELG 07' as herein illustrated and described.

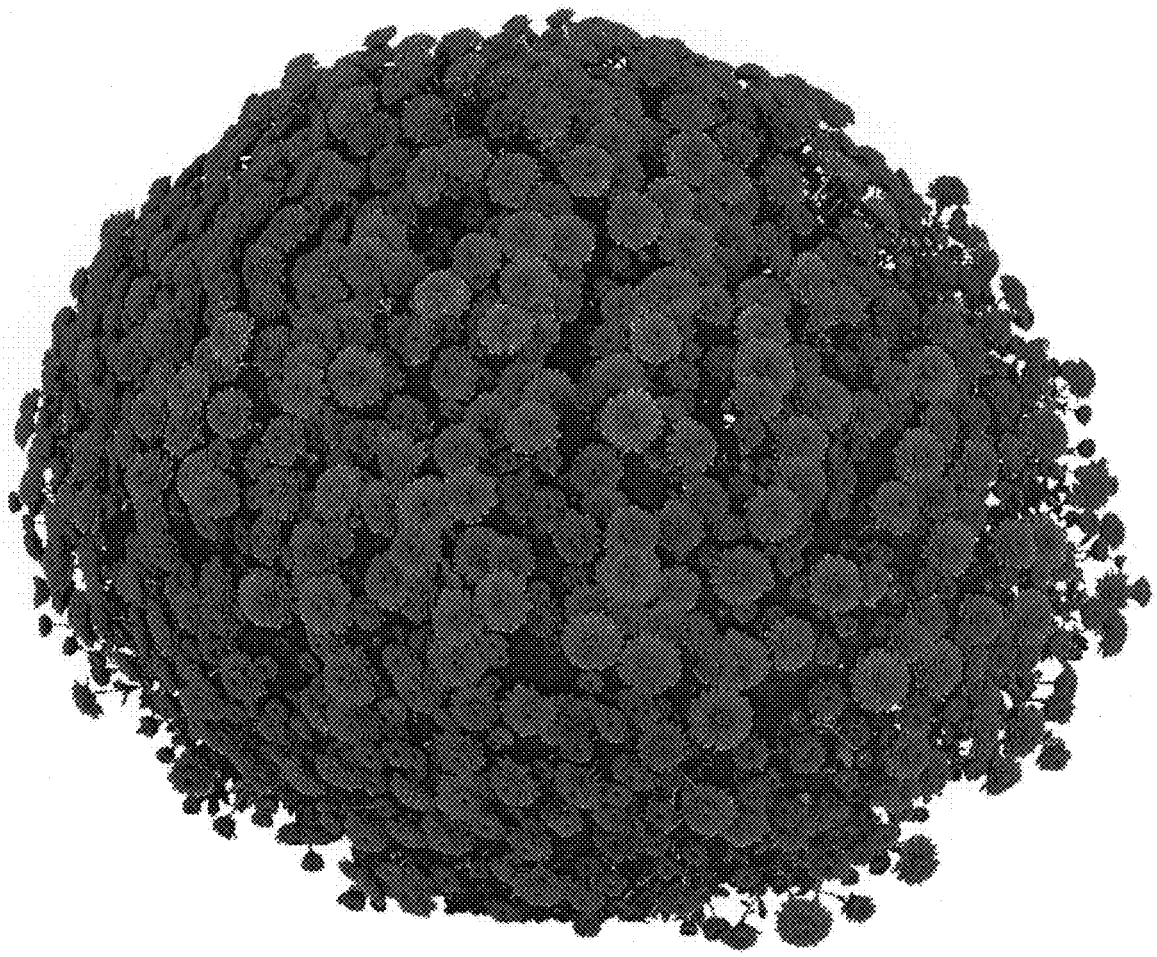

* * * * *